United States Patent
Fruendt et al.

(10) Patent No.: US 10,512,773 B2
(45) Date of Patent: Dec. 24, 2019

(54) ELONGATED GUIDE SHEATH

(71) Applicant: BIOTRONIK SE & Co. KG, Berlin (DE)

(72) Inventors: Carsten Fruendt, Berlin (DE); Erik Trip, Singapore (SG)

(73) Assignee: BIOTRONIK SE & Co. KG, Berlin (DE)

( * ) Notice: Subject to any disclaimer, the term of this patent is extended or adjusted under 35 U.S.C. 154(b) by 99 days.

(21) Appl. No.: 15/317,298

(22) PCT Filed: May 20, 2015

(86) PCT No.: PCT/EP2015/061049
§ 371 (c)(1),
(2) Date: Dec. 8, 2016

(87) PCT Pub. No.: WO2015/193047
PCT Pub. Date: Dec. 23, 2015

(65) Prior Publication Data
US 2017/0100579 A1    Apr. 13, 2017

(30) Foreign Application Priority Data

Jun. 17, 2014  (DE) .................. 10 2014 108 475

(51) Int. Cl.
*A61M 25/06*    (2006.01)
*A61M 25/10*    (2013.01)
(Continued)

(52) U.S. Cl.
CPC ......... *A61N 1/056* (2013.01); *A61M 25/0108* (2013.01); *A61M 25/0127* (2013.01);
(Continued)

(58) Field of Classification Search
CPC ... A61N 1/056; A61M 25/0108; A61M 25/10; A61M 25/0127; A61M 25/0662; A61M 25/09041
See application file for complete search history.

(56) References Cited

U.S. PATENT DOCUMENTS 4,602,645 A * 7/1986 Barrington ............. A61N 1/368
607/123
5,441,504 A * 8/1995 Pohndorf .......... A61M 25/0668
604/164.05
(Continued)

FOREIGN PATENT DOCUMENTS

DE   10 2011 050 173 A1   11/2012
EP    1 806 160 A1        11/2007
WO    2005112798 A2       12/2005

OTHER PUBLICATIONS

Notification of Transmittal of the International Search Report and the Written Opinion of the International Searching Authority, International Search Report and Written Opinion of the International Searching Authority for PCT/EP2015/061049, dated Aug. 12, 2015 (10 pages).

*Primary Examiner* — Tuan V Nguyen
(74) *Attorney, Agent, or Firm* — Buchanan Ingersoll & Rooney PC

(57) ABSTRACT

An elongated guide sheath for delivering at least one medical instrument to a body lumen. For reliable and cost effective implantation of an electrode at the AV septum the inventive guide sheath forms a first guiding sleeve and a second guiding sleeve at least partly separated by a shared wall section, wherein the longitudinal axis of the first guiding sleeve and the longitudinal axis of the second guiding sleeve run parallel to a longitudinal guide sheath axis, wherein the wall of the first guiding sleeve and/or of the second guiding sleeve each comprises a slit which runs
(Continued)

along at least part of the length of the respective guiding sleeve. Further, a system including the above guide sheath, a first catheter and/or guide wire and a second catheter or electrode is proposed.

8 Claims, 16 Drawing Sheets

(51) Int. Cl.
  *A61N 1/05* (2006.01)
  *A61M 25/09* (2006.01)
  *A61N 1/372* (2006.01)
  *A61M 25/01* (2006.01)

(52) U.S. Cl.
  CPC .. *A61M 25/0662* (2013.01); *A61M 25/09041* (2013.01); *A61M 25/10* (2013.01); *A61N 1/372* (2013.01); *A61M 25/0113* (2013.01); *A61M 2025/0188* (2013.01)

(56) References Cited

U.S. PATENT DOCUMENTS

| | | | | |
|---|---|---|---|---|
| 6,544,270 | B1* | 4/2003 | Zhang | A61N 1/056 604/264 |
| 6,928,313 | B2* | 8/2005 | Peterson | A61N 1/056 600/374 |
| 7,570,981 | B2 | 8/2009 | Peterson | |
| 8,142,446 | B2* | 3/2012 | Shan | A61M 39/0693 604/167.01 |
| 2004/0147826 | A1* | 7/2004 | Peterson | A61N 1/056 600/374 |
| 2006/0247750 | A1* | 11/2006 | Seifert | A61N 1/056 607/122 |
| 2008/0009770 | A1* | 1/2008 | Weber | A61F 2/95 600/585 |
| 2008/0015625 | A1 | 1/2008 | Ventura et al. | |
| 2008/0082136 | A1* | 4/2008 | Gaudiani | A61B 17/3468 607/9 |
| 2009/0198252 | A1* | 8/2009 | Seifert | A61N 1/056 606/129 |
| 2011/0301684 | A1* | 12/2011 | Fischell | A61M 25/0662 623/1.11 |

\* cited by examiner

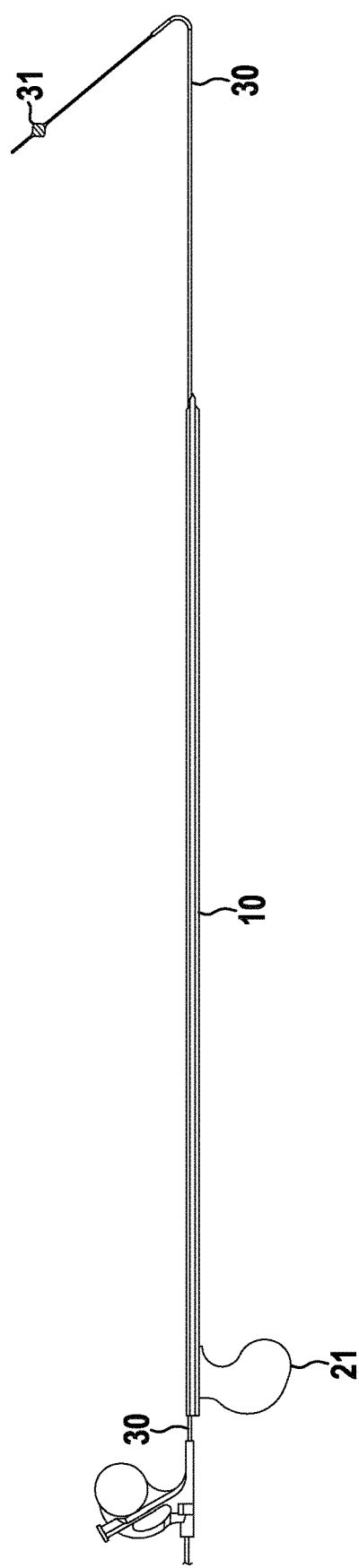

ELONGATED GUIDE SHEATH

CROSS-REFERENCE TO RELATED APPLICATIONS

This application is the U.S. national phase under 35 U.S.C. § 371 of PCT International Patent Application No. PCT/EP2015/061049, filed on May 20, 2015, which claims the benefit of German Patent Application No. DE 10 2014 108 475.6, filed Jun. 17, 2014, the disclosures of which are hereby incorporated by reference herein in their entireties.

TECHNICAL FIELD

The present invention relates to an elongated guide sheath for delivering at least one medical instrument to a body lumen.

BACKGROUND OF THE INVENTION

Minimally invasive procedures have been implemented in a variety of medical settings, e.g., for vascular interventions, such as angioplasty, stenting, embolic protection, electrical heart stimulation, heart mapping and visualization, and the like. These procedures generally rely on accurately navigating and placing instruments within a patient's vasculature. During such procedures, guide wires are used to advance catheters, sheaths or similar medical devices into a patient's body vessel.

Document U.S. Pat. No. 7,570,981 B2 discloses a complex guiding catheter system for accessing a patient's heart.

In order to stimulate the right atrium and the left ventricle of the human heart the Atrioventricular Septum (AV septum) of the heart can be used. Such a dual chamber stimulation is nowadays very common and corresponds to a greater extend to the physiological behaviour of the human heart than other stimulation methods. For such a stimulation usually an electrode is used which comprises an elongated helix construction at its distal end which needs to be exactly positioned at the AV septum.

It is possible to observe the movement of the electrode during implantation and to place the electrode exactly at the AV septum using an ultrasonic system for localization of the electrode tip. However, such an ultrasonic monitoring needs (beside the implantation of the electrode) another intervention which is usually started at the groin. However, this second intervention causes extra stress for the patient and requires another physician during the surgery. This is therefore an expensive, complicated method which does not conform to standard methods in this medical area.

The present invention is directed toward overcoming one or more of the above-mentioned problems.

SUMMARY OF THE INVENTION

Therefore, it is an object of the present invention to provide a system which is able to locate the AV septum easily and cost effectively.

At least the above problem is solved by an elongated guide sheath for delivering at least one medical instrument to a body lumen, wherein the sheath forms a preferably cylindrical and elongated first guiding sleeve and a preferably cylindrical and elongated second guiding sleeve at least partly separated by a shared wall section, wherein the longitudinal axis of the first guiding sleeve and the longitudinal axis of the second guiding sleeve run parallel to a longitudinal guide sheath axis, wherein the wall of the first guiding sleeve and/or of the second guiding sleeve comprises a slit which runs along at least part of the length of the respective guiding sleeve.

The inventive elongated guide sheath is of advantage because it is possible according to the present invention to first introduce a first catheter or a guide wire, preferably comprising a retaining element, and to temporarily fix the catheter or guide wire at the sinus coronarius for orientation, preferably using an inflated balloon. Then, the elongated guide sheath is inserted along the fixed first catheter or guide wire, wherein the first catheter or guide wire is accommodated within the first guiding sleeve. After that along the second guiding sleeve of the guide sheath a second catheter comprising the electrode for stimulation of the AV septum or a respective electrode is inserted and implanted at the AV septum using the catheter or guide wire fixed within the sinus coronarius as orientation. Thereby, an easy and cost effective implantation of an electrode at the AV septum is provided. No more additional ultrasonic monitoring is necessary. Accordingly, a second intervention for ultrasonic monitoring is avoided.

The inner diameter of the first guiding sleeve and/or the second guiding sleeve of the inventive guide sheath is preferably between 0.3 mm and 5 mm, more preferred between 0.5 mm and 3 mm. The wall thickness of the first guiding sleeve and the second guiding sleeve is preferably between 0.1 mm and 0.5 mm, more preferred between 0.2 mm and 0.3 mm.

The slit within the wall of the first guiding sleeve and/or of the second guiding sleeve is through going and allows accommodation of the first catheter and/or the second catheter and/or the guide wire within the guide sheath and/or easy removal. Further, the first guiding sleeve and the second guiding sleeve are accommodated beside each other.

In a preferred embodiment the slit in the wall of at least the first guiding sleeve and/or the second guiding sleeve extends over the entire length of the respective guiding sleeve which simplifies the step of clipping the sheath on the first catheter or guide wire and further eases removal of the guide sheath after implantation of the electrode.

It is further advantageous because of the same reason if the slit of the first guiding sleeve and/or the slit of the second guiding sleeve run at least sectionally parallel to the longitudinal guide sheath axis. In a further embodiment the slit of the second guiding sleeve is accommodated opposite to the slit of the first guiding sleeve in the respective outer wall.

In a preferred embodiment at its proximal end the guide sheath comprises a handle for rotation of the sheath around the longitudinal sheath axis or parallel thereto. This handle further facilitates implantation of the electrode at the AV septum.

A further embodiment of the inventive guide sheath comprises a tip at its distal end, preferably mainly formed by the shared wall section. This tip allows easier introduction of the longitudinal sheath into the vasculature. In a preferred embodiment, the walls of the first guiding sleeve and the second guiding sleeve are beveled at their distal end forming the tip.

It is further of advantage if the shared wall section separates the first guiding sleeve and the second guiding sleeve completely in order to reduce interaction between a guide wire or a to first catheter accommodated within the first guiding sleeve and a second catheter or electrode accommodated in the second guiding sleeve.

In order to monitor the position of the guide sheath the inventive guide sheath preferably comprises at its distal end, for example within or at the wall of the first guiding sleeve is and/or the second guiding sleeve, an X-ray visible element (marker) or magnetic element (marker). Preferably, the X-ray visible element has the form of a stripe. The X-ray visible element absorbs a larger amount of the impinging X-rays than the vicinity of this element within the human body during surgery and is therefore visible.

As indicated above in a preferred embodiment the first guiding sleeve is adapted to receive a first catheter and/or a guide wire, each preferably comprising a retaining element, for example an inflatable balloon or a clamp.

In a further preferred embodiment, the second guiding sleeve is adapted to receive a second catheter, preferably with an electrode, or an electrode.

At least the above problem is further solved with the same advantages by a system comprising an elongated guide sheath as described above, a first catheter and/or guide wire, each preferably comprising a retaining element, and a second catheter, preferably comprising an electrode, or an electrode.

Each of the above mentioned first and second catheters preferably comprises a catheter shaft and a connecting element for connection with the catheter control. The second catheter preferably accommodates at least one electrode with a respective connecting lead within its shaft. The first catheter preferably comprises a balloon at its distal end as the retaining element wherein the balloon may be inflated and deflated using a fluid supply accommodated within the catheter.

In order to remove the second catheter without removing or loosening the implanted electrode at the AV septum the system further preferably comprises a slitter.

A full and enabling disclosure of the present invention, including the best mode thereof, directed to one of ordinary skill in the art is set forth in the following specification of the preferred embodiments. Thereby, further features and advantages are presented that are part of the present invention independently of the features mentioned in the dependent is claims.

Further features, aspects, objects, advantages, and possible applications of the present invention will become apparent from a study of the exemplary embodiments and examples described below, in combination with the figures, and the appended claims.

DETAILED DESCRIPTION OF THE INVENTION

In FIGS. 1 to 11, a first embodiment of an inventive system with a first embodiment of an elongated guide sheath 10 is shown. Further, the treatment of the patient using this system is described in the following.

Figure 5:
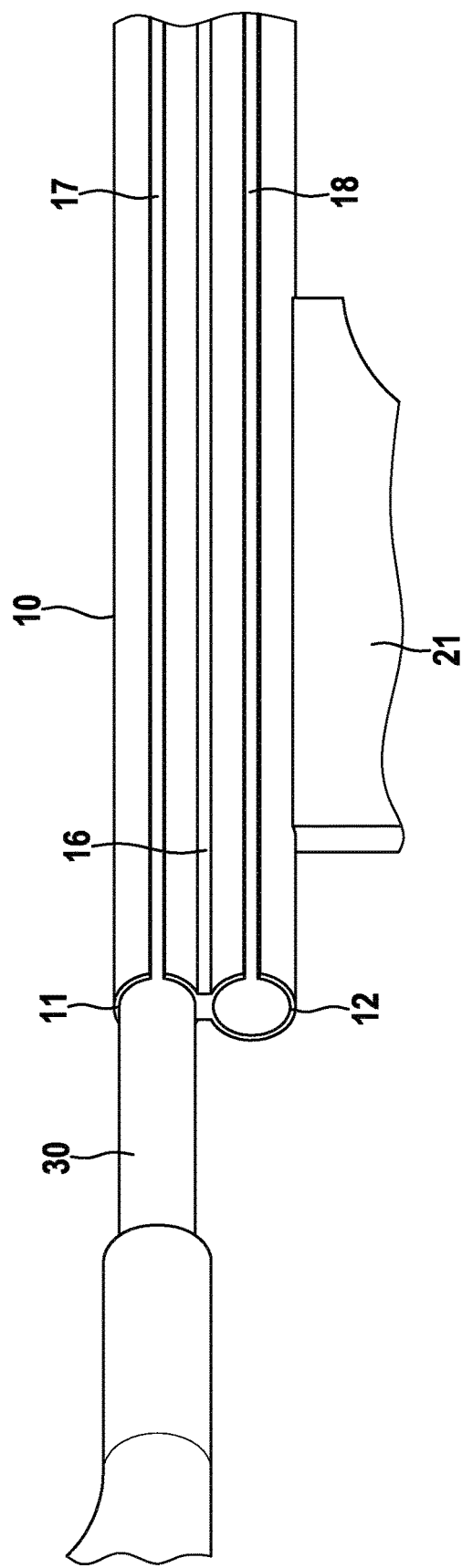
Figure 6:
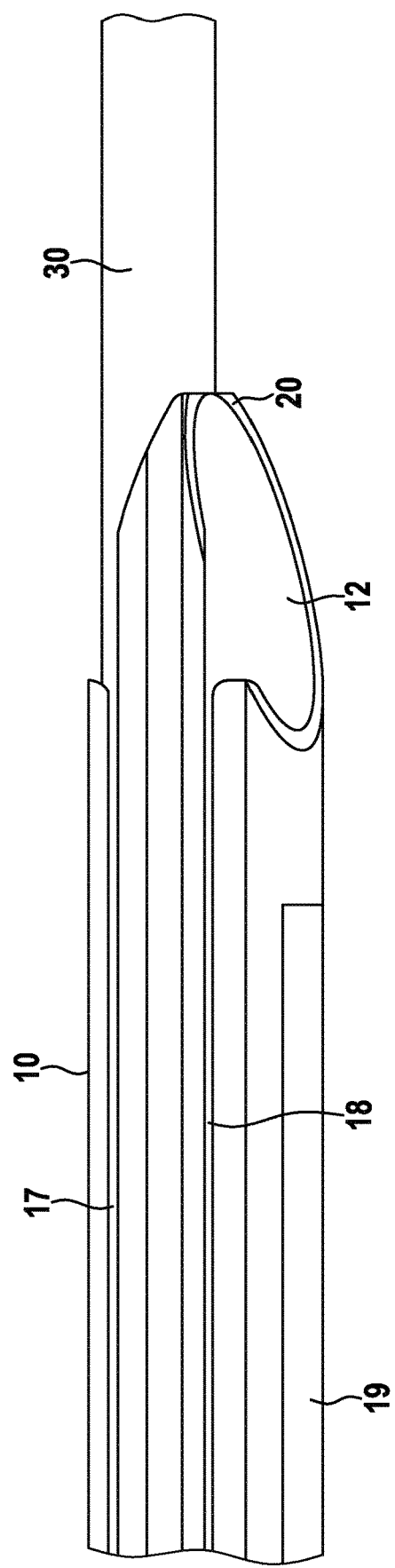
Figure 7:
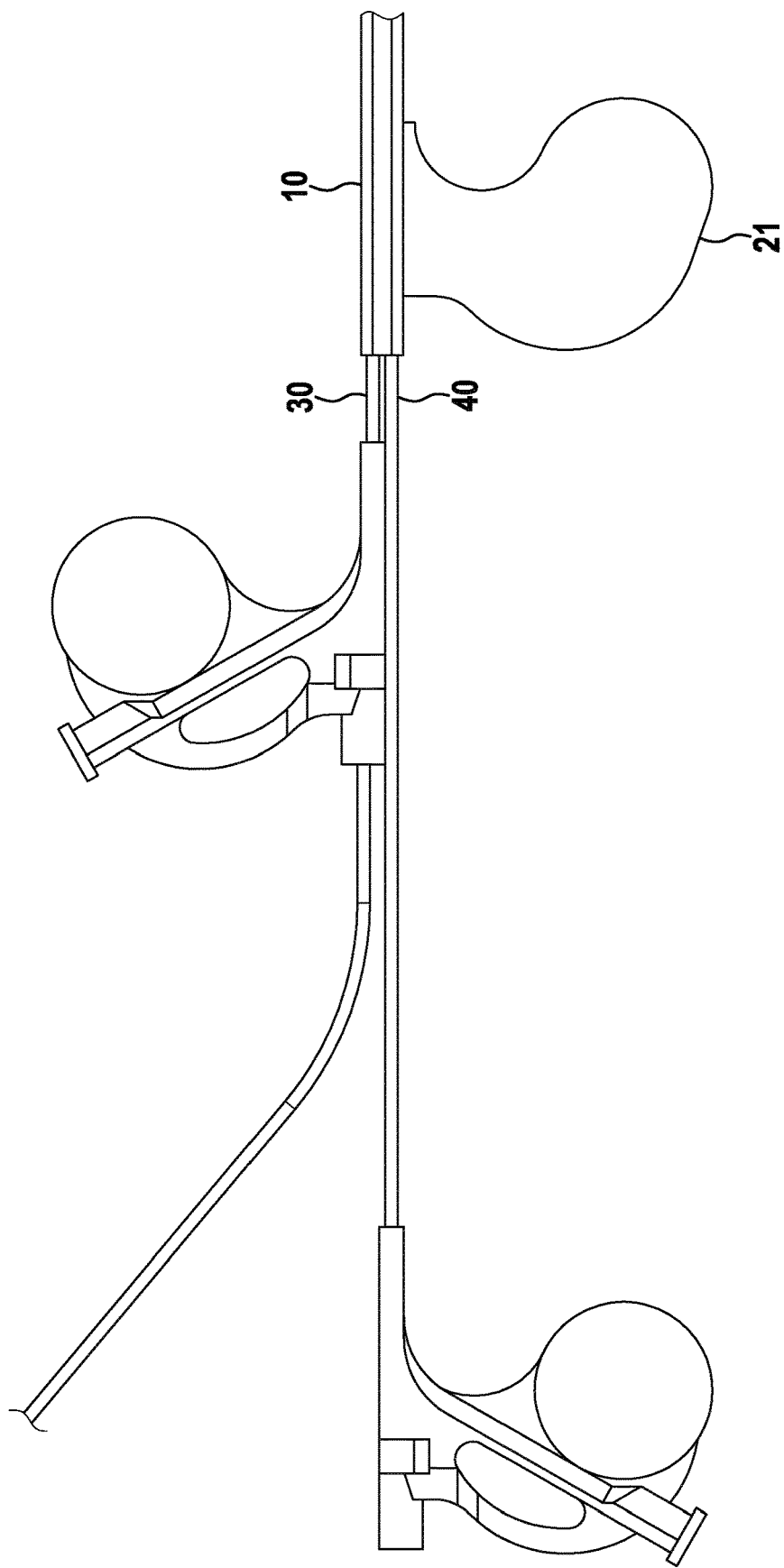
Figure 8:
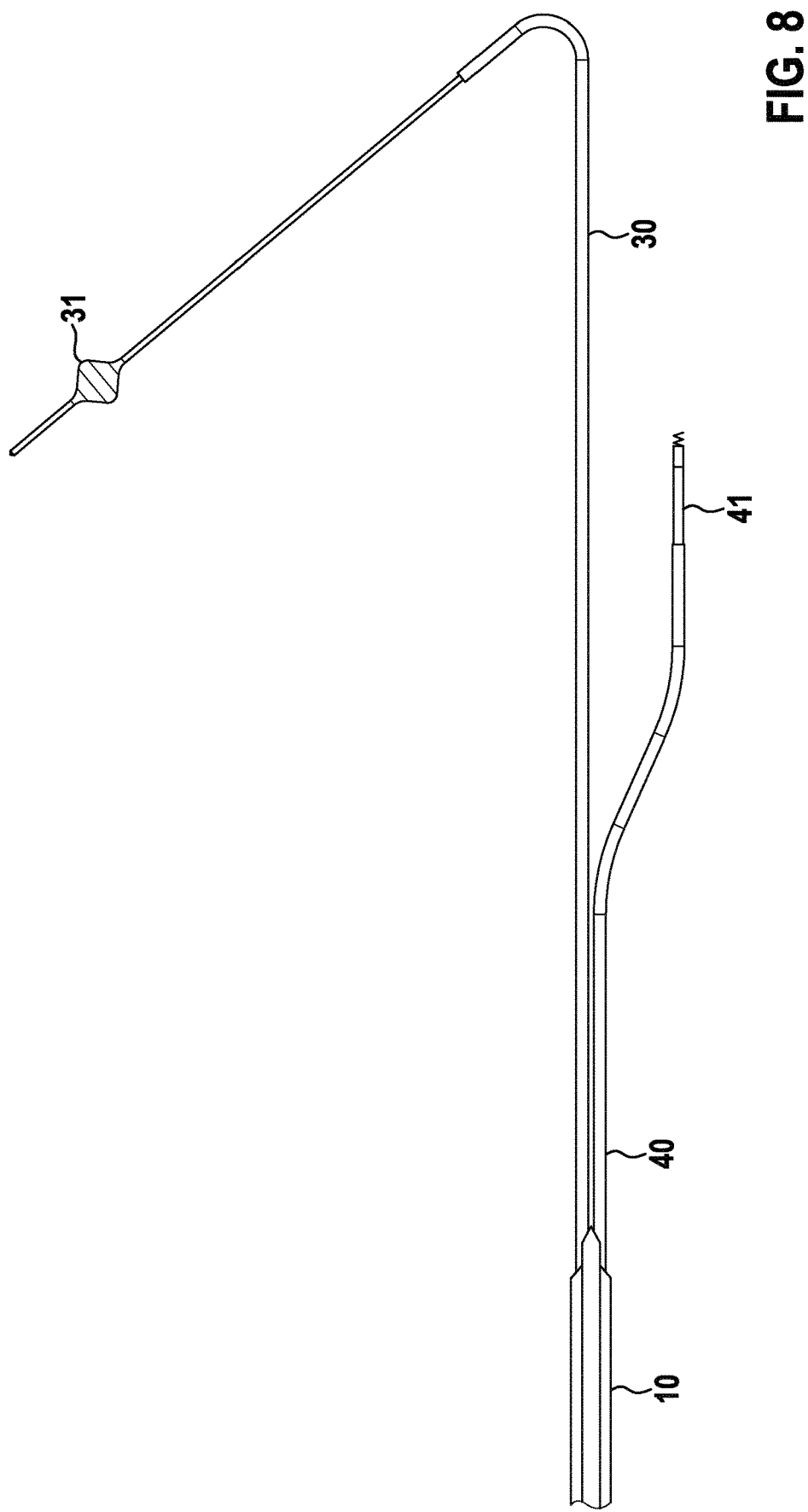

The first embodiment of the inventive guide sheath 10 comprises an elongated body with a first cylindrical guiding sleeve 11 and a second cylindrical guiding sleeve 12. Each guiding sleeve 11, 12 has for example an inner diameter of about 1.83 mm and a wall thickness of about 0.24 mm. Hence, a 5 F (French) catheter may be accommodated by each sleeve 11, 12. The first guiding sleeve 11 and the second guiding sleeve 12 are accommodated in parallel beside each other such that the longitudinal sheath axis 14 runs parallel to the longitudinal axis (not shown) of the first guiding sleeve 11 and the longitudinal axis (not shown) of the second guiding sleeve 12. As best seen in FIG. 5 the first guiding sleeve 11 and the second guiding sleeve 12 are completely separated but connected by a shared wall section 16 which preferably runs along the entire length of the guide sheath 10. Within its side wall the first guiding sleeve 11 comprises a through going first slit 17 which runs along the whole length of the guide sheath 10 and thereby of the first guiding sheath 11. Analogously, the second guiding sleeve 12 comprises a through going second slit 18 in its side wall opposite to the first slit 17 wherein the slit 18 runs parallel to the longitudinal sheath axis 14 preferably along the whole length of the sheath 10 or the second guiding sleeve 12. At the outer surface of the wall or within the wall of the second guiding sleeve 12 the guide sheath 10 comprises an X-ray visible element 19 which has the form of an elongated stripe.

The X-ray visible element 19 may be realized by a single stripe or a plurality of stripes or patches.

Figure 2:
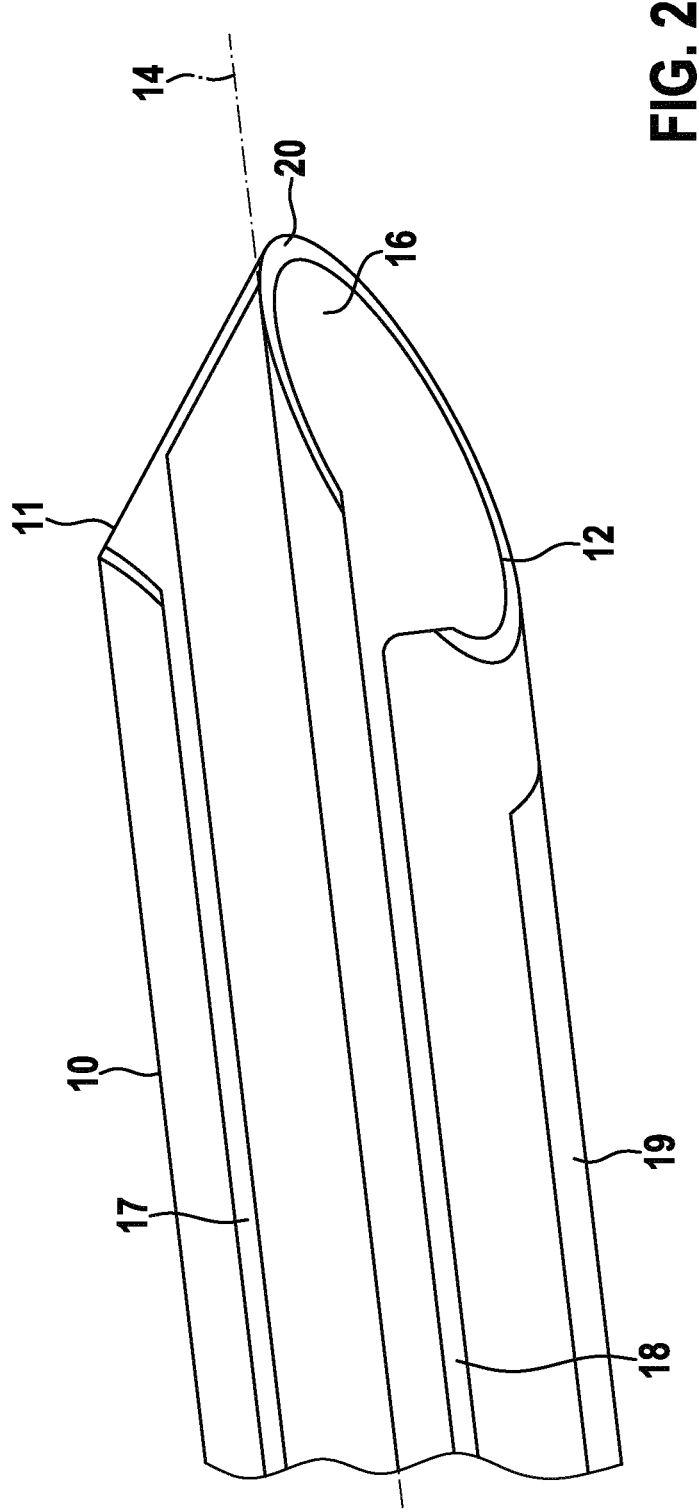

At the distal end of the inventive guide sheath 10 as best shown in FIG. 2 the beveled walls of the first guiding sleeve 11 and the second guiding sleeve 12 form a tip 20. The distal end of the tip 20 is formed by the shared wall 16.

The guide sheath 10 further comprises at its proximal end a handle 21 that is fixed at the outer surface of the second guiding sleeve 12 for example (see FIGS. 4, 4a, 5 and 7).

Figure 1:
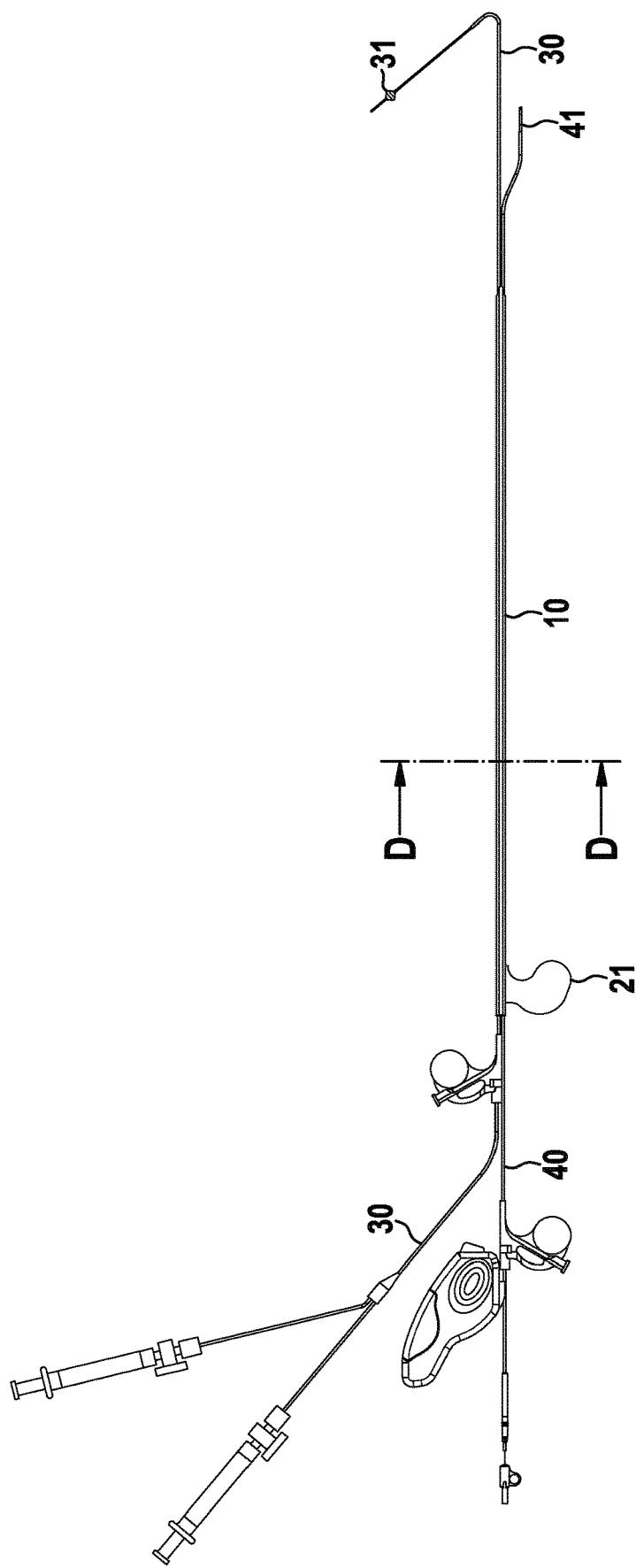
FIG. 1 a first embodiment of an inventive system comprising a first and a second catheter and a first embodiment of an inventive guide sheath in a side view, FIG. 2 a distal end section of the inventive guide sheath according to the embodiment of FIG. 1 in a side view, FIG. 3 a first catheter representing a first step of a surgical method for implantation of an electrode in the AV septum in a side view, FIGS. 4 and 4a the first catheter and the inventive guide sheath according to the embodiment of FIG. 1 representing a second step of the surgical method in a side view and in a perspective view with the guide sheath partially introduced into a patient's body, FIG. 5 a first detail of FIG. 4 showing a proximal portion of the first catheter and a proximal end section of the inventive guide sheath according to the embodiment of FIG. 1, FIG. 6 a second detail of FIG. 4 depicting the distal end section of the inventive guide sheath according to the embodiment of FIG. 1 and a distal portion of the first catheter, FIG. 7 a proximal portion of the first catheter, the proximal end section of the inventive guide sheath according to the embodiment of FIG. 1 and a proximal portion of a second catheter representing a third step of the surgical method in a side view, FIG. 8 the distal end portion of the first catheter, the distal end section of the inventive guide sheath according to the embodiment of FIG. 1 and a distal end portion of the second catheter representing the third step of the surgical method (also shown in FIG. 7) in a side view, FIG. 9 a cross section of the human heart showing the arrangement of the distal end of the first and of the second catheter as well as of the inventive guide sheath, FIG. 10 the system of FIG. 7 with removed inventive guide sheath in a side view, FIG. 11 the proximal end portion of the second catheter in further step of the method with a slitter in a side view, FIG. 12 a second embodiment of an inventive system comprising a first and a second catheter, a slitter and a second embodiment of an inventive guide sheath in a side view, FIG. 13 the inventive guide sheath according to the embodiment of FIG. 12 in a cross section along the line A-A (see FIG. 12), FIG. 14 a third embodiment of an inventive system comprising a second catheter, a slitter and a third embodiment of an inventive guide sheath in a side view, and FIG. 15 the cross section of the inventive guide sheath according to FIG. 14 along the line B-B (see FIG. 14).

Now, the method for implantation of an electrode at the AV septum using the inventive guide sheath 10 and the inventive system of FIG. 1, respectively, will be described referring to FIGS. 3 to 11. In these Figures the patient's body 5 is only shown in FIG. 4a and in FIG. 9, where a cross section of the patient's heart 50 is depicted.

Figure 3:
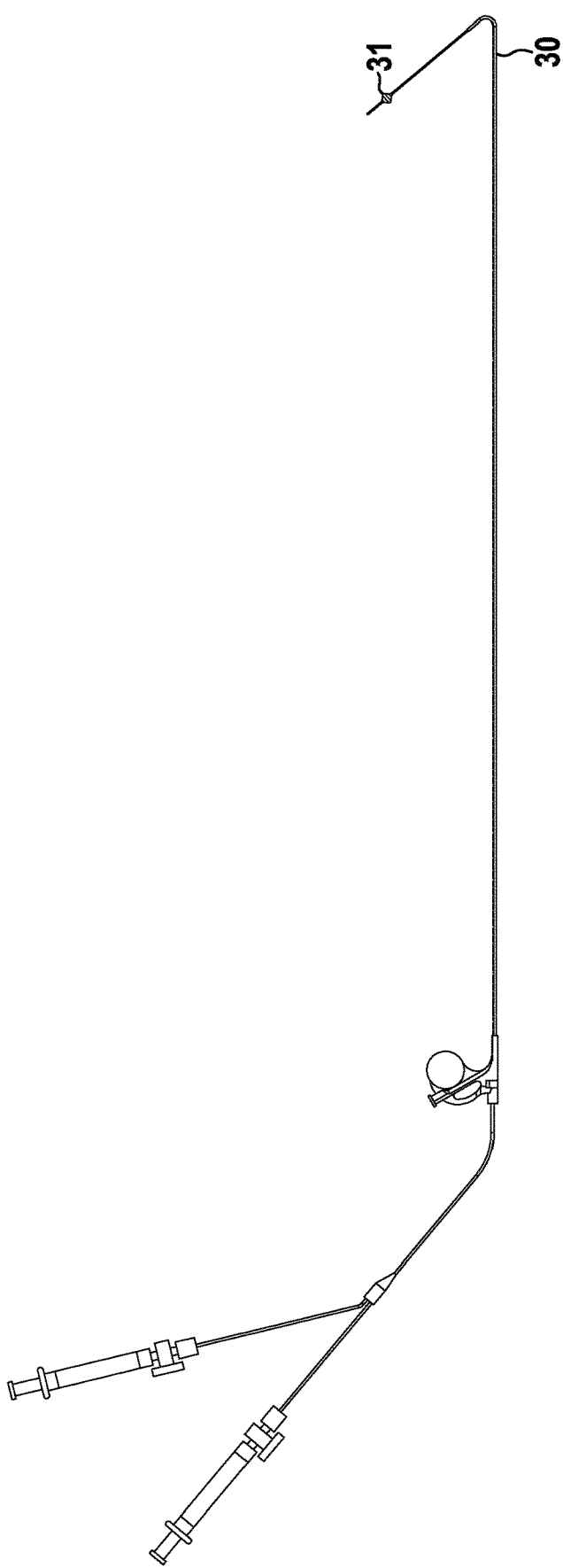
Figure 9:
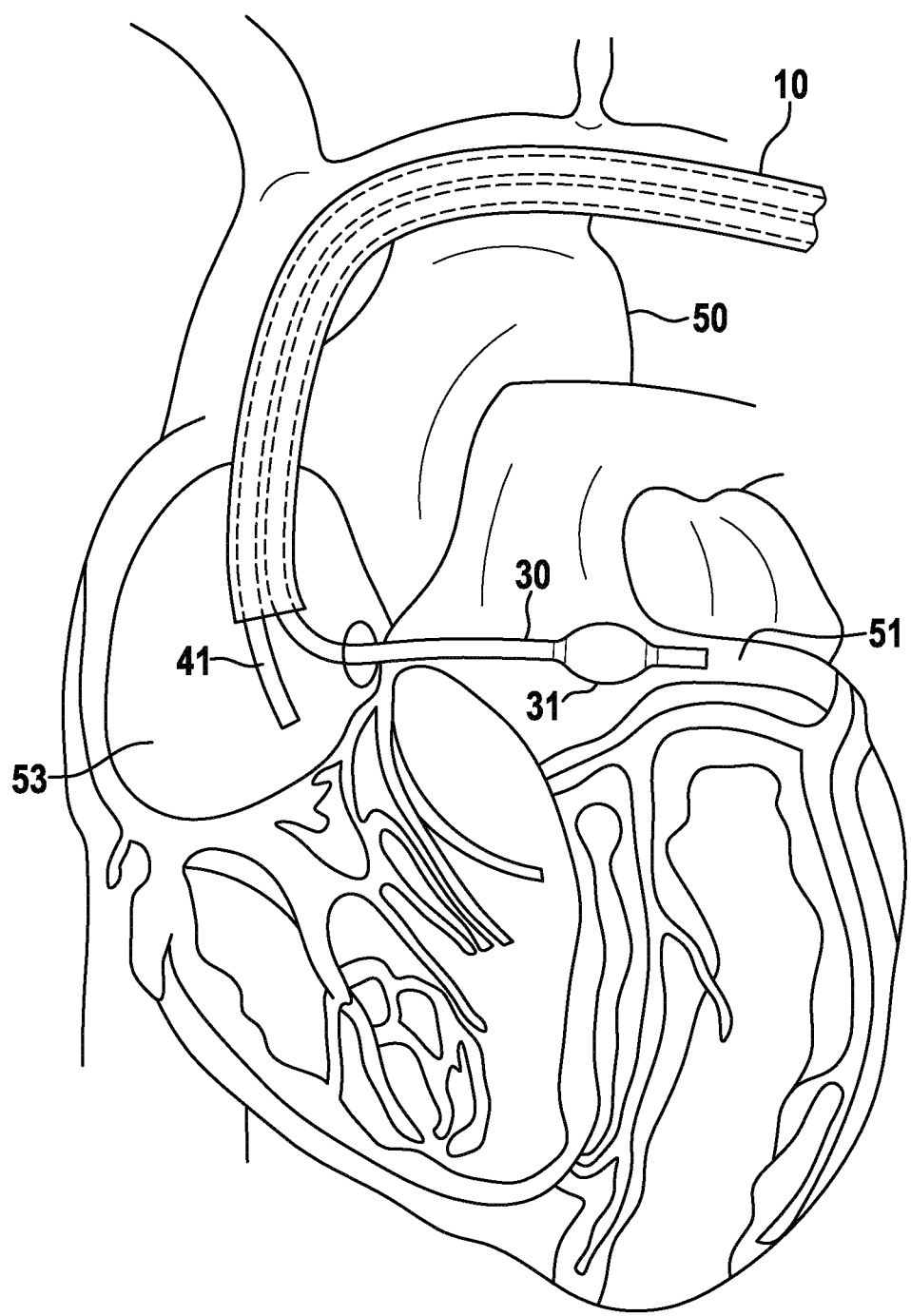

In a first step the first catheter 30 shown in FIG. 3 is inserted into the vasculature of the patient according to the usual procedure and is advanced such that the distal end of the first catheter 30 is located at the sinus coronarius 51 and temporarily fixed therein, for example by inflating a balloon 31 accommodated at the distal end of the first catheter 30 (perfusion). Therefore, preferably a balloon catheter is used. Alternatively, a locking guide wire or a normal guide wire may be used comprising a retaining element at its distal end. The location of the distal end of the first catheter 30 within the heart 50 at the end of the first method step is shown in FIG. 9.

Figure 4A:
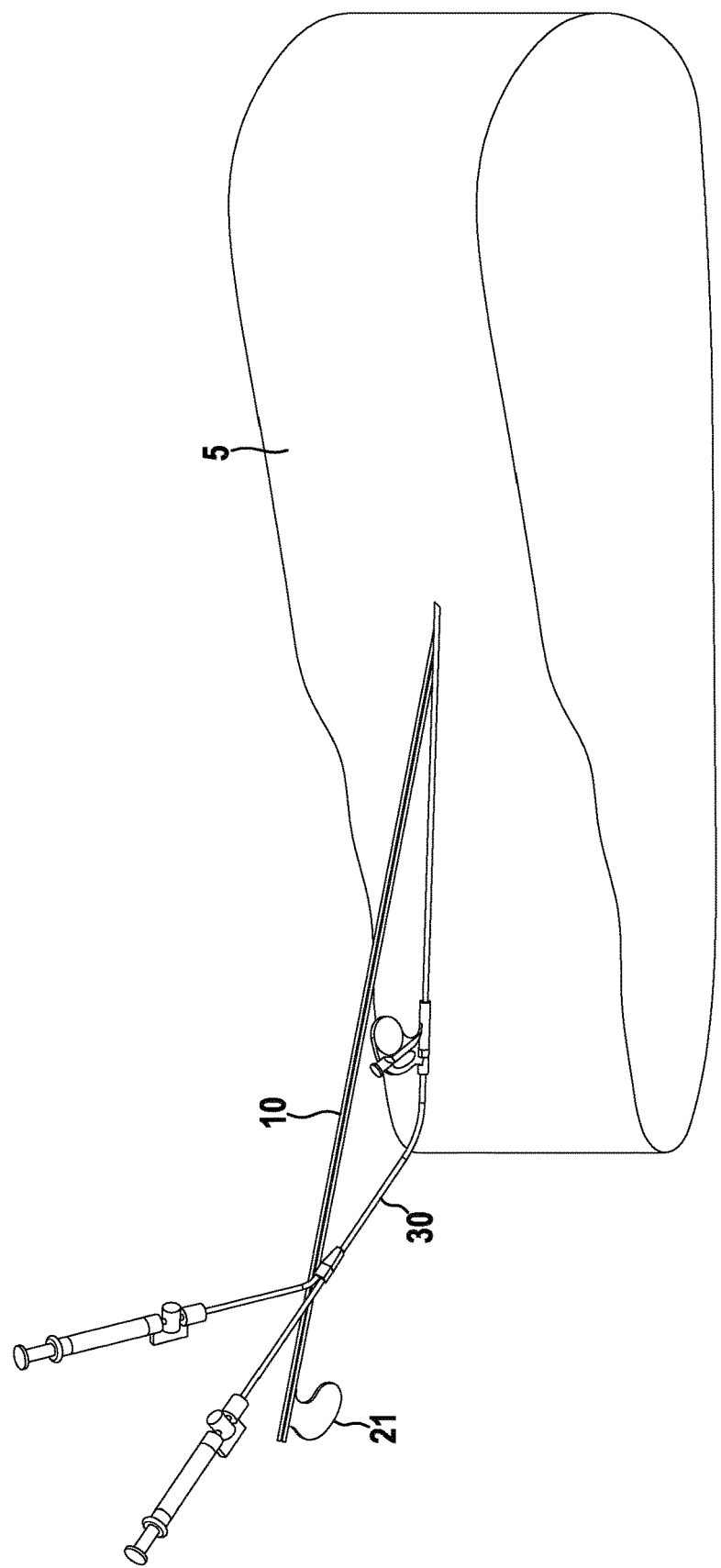

In the second step, at the proximal end of the first catheter 30 which projects from the patient's body 5 (ref. FIG. 4a) the inventive guide sheath 10 is clipped around the first catheter 30 using the first slit 17 such that the first catheter 30 is accommodated within the first guiding sleeve 11 (see FIGS. 5, 6). Using the first catheter 30 as a guide the guide sheath 10 is inserted into the vasculature and advanced until a predetermined position is reached within the heart 50 and with regard to the position of the first catheter 30 (see FIG. 9). The correct position of the distal end of the guide sheath 10 can be determined using the X-ray visible element 19.

Then, a second catheter 40 containing an electrode 41 with its connecting lead or alternatively an electrode is inserted within the second guiding sleeve 12 of the inventive guide sheath 10 (see FIGS. 7 and 8) and advanced within the guide sheath 10 until the interior of the heart 50 is reached. Now or prior to insertion of the electrode the guide sheath 10 is rotated around the guide sheath axis 14 or parallel thereto using the handle 21. After that, the electrode 41 at the distal end of the second catheter 40 is properly positioned at the AV septum 53 (see FIG. 9) and implanted, i.e. fixed, there.

Figure 10:
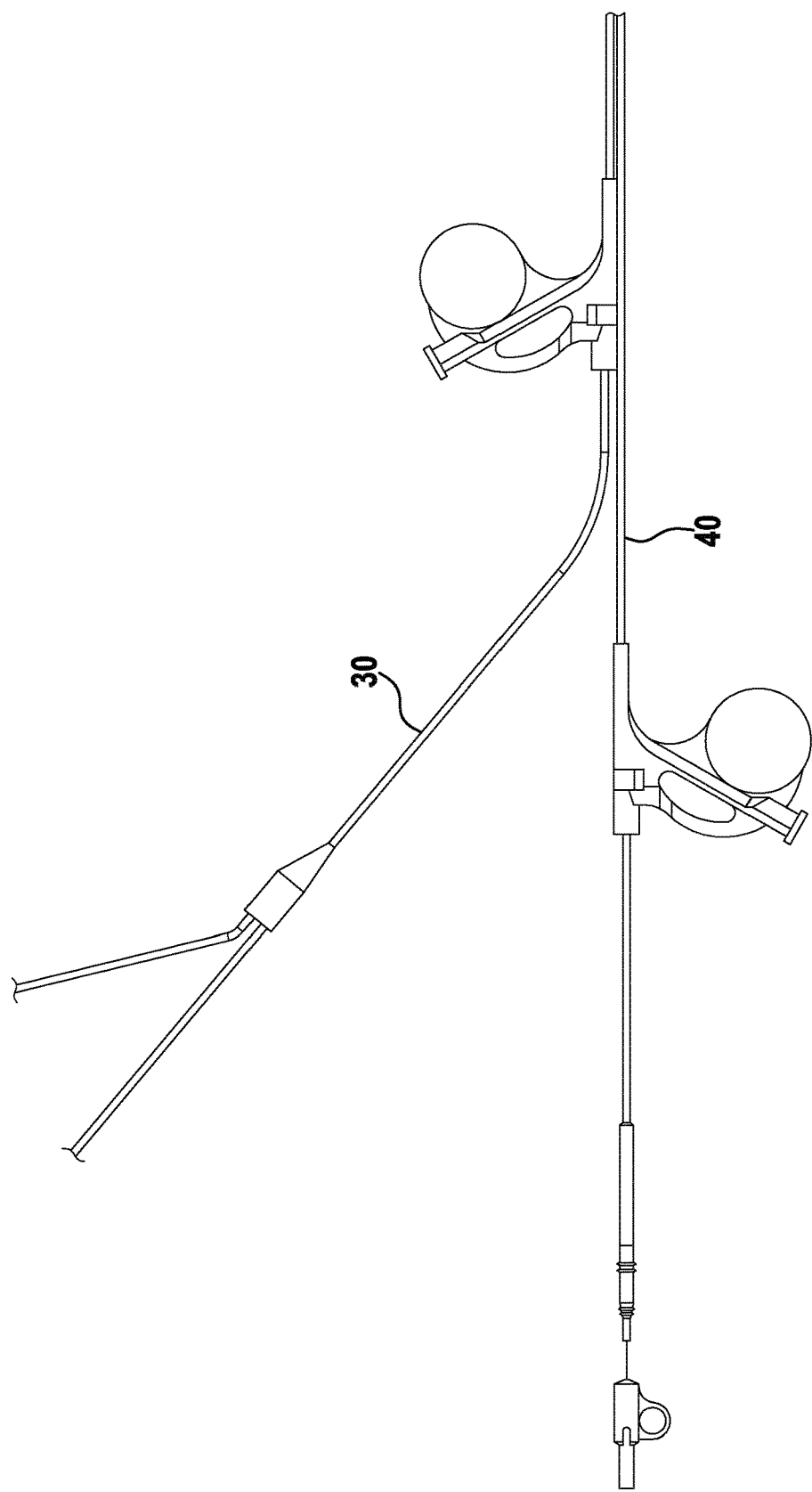
Figure 11:
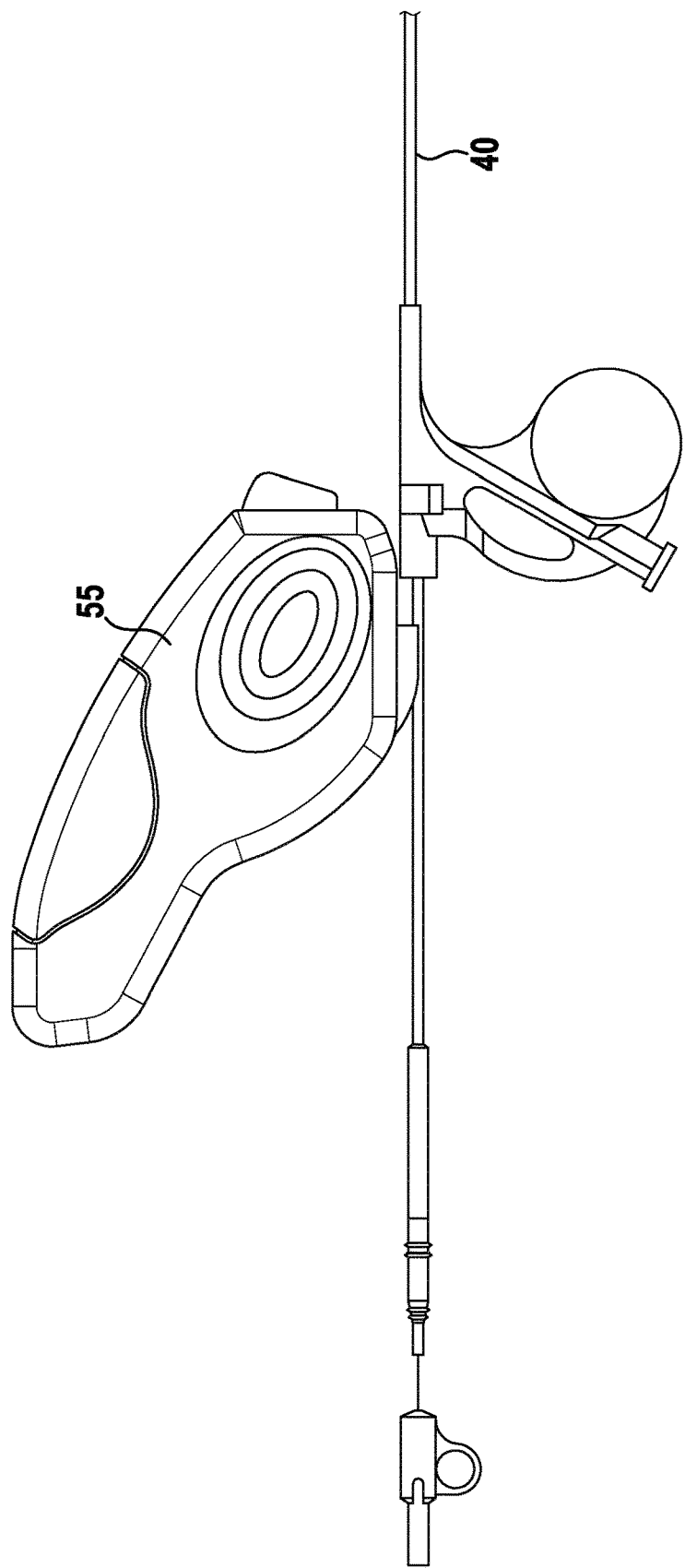

Now, the guide sheath 10 is unclipped from the first catheter 30 and second catheter 40 by means of the first slit 18 and the second slit 19 and removed from the vasculature of the patient. Then, the first catheter 30 is removed after the temporary fixation of the first catheter within the sinus coronaries 51 is released, for example by deflation of the balloon 31. This step is shown in FIG. 10.

Then, the shaft of the second catheter 40 is removed from the patient's body using a slitter 55 (see FIG. 11), wherein the electrode 41 stays fixed at the AV septum 53.

As the skilled person derives from the above explanation the inventive guide sheath 10 allows an easy and cost effective as well as exact location and implantation of an electrode at the AV septum 53. An additional ultrasonic monitoring system is not necessary.

Figure 12:
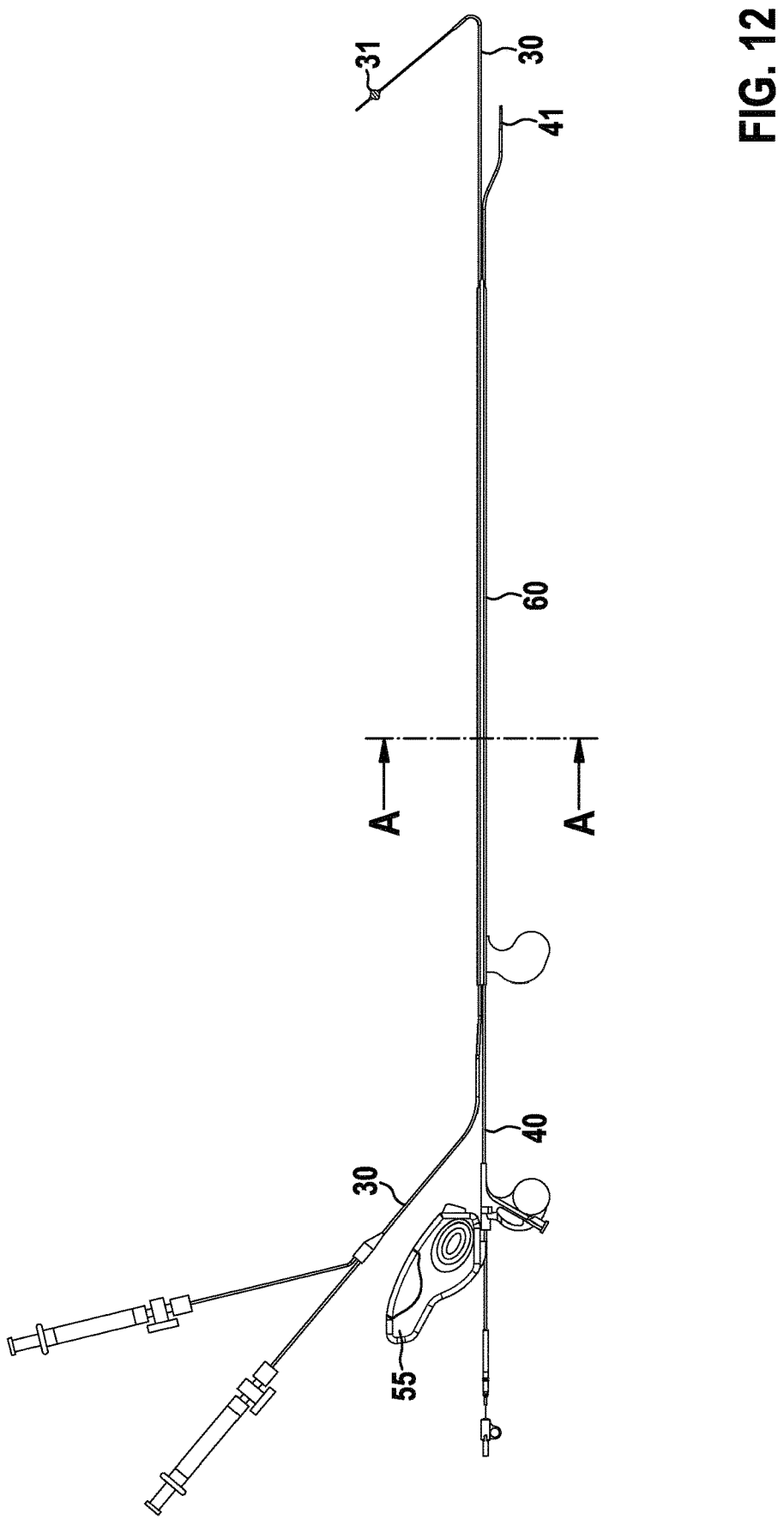

FIG. 12 shows a second embodiment of an inventive system with a first catheter 30, a second catheter 40, a slitter 55 and a second embodiment of a guide sheath 60. The guide sheath 60 comprises a first guiding sleeve 61 with a slit 17 and a second guiding sleeve 62 which are not fully separated as in the first embodiment of the guide sheath 10. Accordingly, the separating wall section 66 of the first guiding sleeve 61 and the second guiding sleeve 62 contains a clearance 67 forming an elongated slit. The second guiding sleeve 62 does not have any slit in its wall. The slit 17 is used for clipping the guide sheath 60 around the first catheter 30 which distal tip is already positioned within the heart as described above. Removal of the second catheter 40 is facilitated by the slitter 55.

The first guiding sleeve 61 has an inner diameter d61 of about 2 mm and the second to guiding sleeve 62 an inner diameter d62 of about 3 mm. The wall thickness w60 of the guide sheath 60 is about 0.1 mm. The height h60 of the guide sheath 60 is about 15 F.

Figure 14:
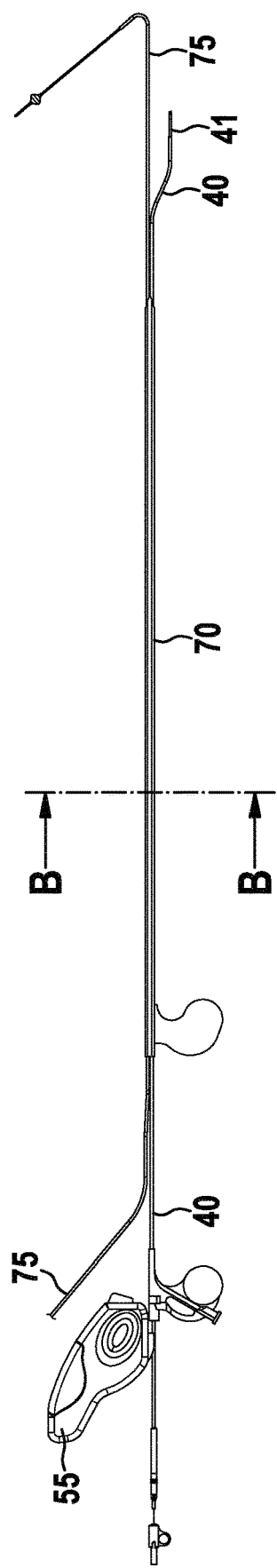

FIG. 14 shows a third embodiment of an inventive system with a second catheter 40, a slitter 55 and a third embodiment of a guide sheath 70.

Figure 15:
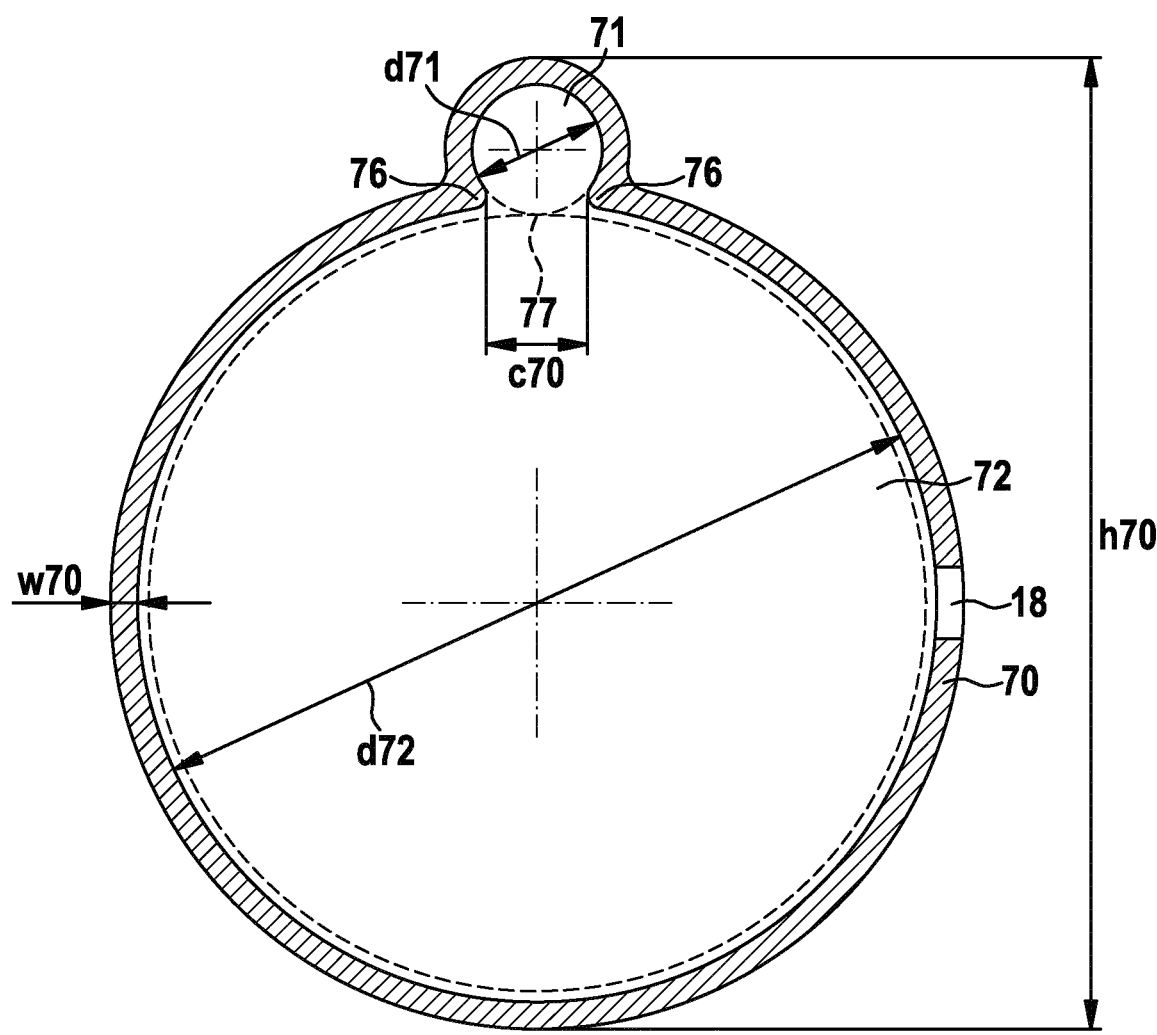

As it can be seen in the cross section depicted in FIG. 15 the guide sheath 70 comprises a first guiding sleeve 71 and a second guiding sleeve 72, wherein the diameter d71 of the first guiding sleeve 71 is much less than the diameter d72 of the second guiding sleeve 72. As examples d71 is about 0.5 mm and d72 is about 3 mm. The first guiding sleeve 71 serves for accommodation of a guide wire 75 rather than a catheter as in the previous embodiments of guide sheaths 10, 60. The wall thickness of the first guiding sleeve 71 and the second guiding sleeve 72 w70 is about 0.1 mm.

Figure 13:
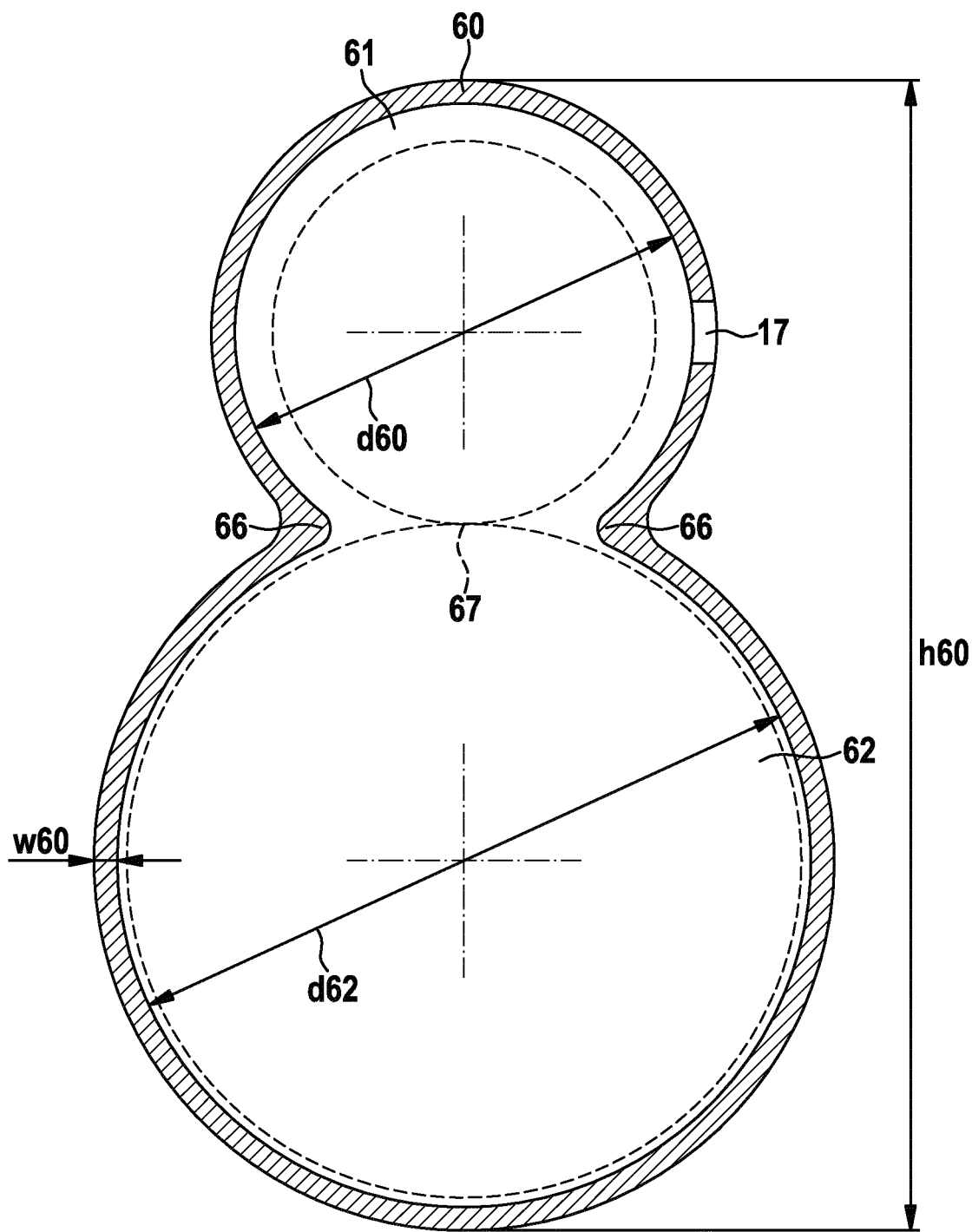

Analogous to the embodiment of FIGS. 12 and 13 the first guiding sleeve 71 and the second guiding sleeve 72 are not fully separated. The wall section 76 of the first guiding sleeve 71 and the second guiding sleeve 72 forms an elongated clearance in the form of a slit 77 therein with a width c70 of about 0.38 mm.

As depicted in FIG. 15, the second guiding sleeve 72 comprises a slit 18 for clipping the guide sheath 70 around the guide wire 75 that is correctly positioned within the patient's heart 50 comparable to the first catheter 30 described with regard to the previous embodiments above. The guide wire 75 is placed within the first guiding sleeve 71 and therefore passes clearance 77. The catheter 40 is then introduced by the known Over-The-Wire Technique (OTW). After positioning of the electrode 41 within the AV septum the catheter 40 is removed using the slitter 55.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof.

REFERENCE NUMBERS 5 patient's body
10 guide sheath
11 first guiding sleeve
12 second guiding sleeve
14 longitudinal axis
16 wall section
17 first slit
18 second slit
19 X-ray visible element 20 tip
21 handle
30 first catheter
31 balloon
40 second catheter
41 electrode
50 patient's heart
51 sinus coronarius
53 AV septum
55 slitter
60, 70 guide sheath
61, 71 first guiding sleeve
62, 72 second guiding sleeve
66, 76 wall section
67, 77 clearance
75 guide wire
c70 width of clearance 77
d61, d62, d71, d72 inner diameter
h60, h70 height
w60, w70 wall thickness

The invention claimed is:

1. System for the implantation of an electrode at the AV septum, comprising:
    a first catheter and/or guide wire, each comprising a retaining element and each configured to temporarily fix the catheter or guide wire at the sinus for orientation;
    a second catheter, comprising an electrode for the stimulation of the AV septum; and
    an elongated guide sheath for delivering at least one medical instrument to a body lumen,
    wherein the elongated guide sheath forms a first guiding sleeve and a second guiding sleeve at least partially separated by a shared wall section,
    wherein the first guiding sleeve is adapted to receive the first catheter and/or the guide wire, and the second guiding sleeve is adapted to receive the second catheter with the electrode,
    wherein a longitudinal axis of the first guiding sleeve and a longitudinal axis of the second guiding sleeve run parallel to a longitudinal guide sheath axis, and
    wherein a through going slit in the wall of at least one of the first guiding sleeve and second guiding sleeve extends over the entire length of the respective guiding sleeve and defines an opening in the respective guiding sleeve extending the entire length thereof.

2. The system according to claim 1, wherein the slit of the first guiding sleeve and/or the slit of the second guiding sleeve run at least sectionally parallel to the longitudinal sheath axis.

3. The system according to claim 1, wherein the elongated guide sheath at its proximal end comprises a handle.

4. The system according to claim 1, wherein the elongated guide sheath comprises a tip at its distal end formed by the shared wall section.

5. The system according to claim 1, wherein the shared wall section separates the first guiding sleeve and the second guiding sleeve completely.

6. The system according to claim 1, wherein the elongated guide sheath comprises at its distal end, within or at the wall of the first guiding sleeve and/or the second guiding sleeve, an X-ray visible element or magnetic element.

7. The system according to claim 1, further comprising a slitter.

8. System for the implantation of an electrode at the AV septum, comprising:
    a first catheter and/or guide wire, each comprising a retaining element and each configured to temporarily fix the catheter or guide wire at the sinus coronarius for orientation;
    a second catheter, comprising an electrode for the stimulation of the AV septum; and
    an elongated guide sheath for delivering at least one medical instrument to a body lumen,
    wherein the elongated guide sheath forms a first guiding sleeve and a second guiding sleeve at least partially separated by a shared wall section,
    wherein the first guiding sleeve is adapted to receive the first catheter and/or the guide wire, and the second guiding sleeve is adapted to receive the second catheter with the electrode,
    wherein a longitudinal axis of the first guiding sleeve and a longitudinal axis of the second guiding sleeve run parallel to a longitudinal guide sheath axis,
    wherein the wall of the first guiding sleeve and/or of the second guiding sleeve comprises a through going slit which runs along at least part of the length of the respective guiding sleeve and defines an opening in the respective guiding sleeve extending said at least part of the length thereof.

* * * * *